United States Patent [19]

Marker

[11] Patent Number: 5,585,527
[45] Date of Patent: Dec. 17, 1996

[54] CONTINUOUS DISTILLATION AND MEMBRANE PROCESS

[75] Inventor: Terry L. Marker, Warrenville, Ill.

[73] Assignee: UOP, Des Plaines, Ill.

[21] Appl. No.: 328,797

[22] Filed: Oct. 31, 1994

[51] Int. Cl.$^6$ ............................. C07C 29/20; C07C 27/26
[52] U.S. Cl. ........................ 568/835; 568/868; 568/913; 568/918
[58] Field of Search .................................. 568/835, 868, 568/913, 918

[56] References Cited

U.S. PATENT DOCUMENTS

| | | | |
|---|---|---|---|
| 4,345,973 | 8/1982 | Ladisch et al. | 203/19 |
| 4,774,365 | 9/1927 | Chen et al. | 568/697 |
| 4,906,787 | 3/1960 | Huang et al. | 568/697 |
| 5,160,046 | 11/1992 | Pasternak | 210/640 |

*Primary Examiner*—Paul J. Killos
*Attorney, Agent, or Firm*—Thomas K. McBride; Eugene I. Snyder; Maryann Maas

[57] ABSTRACT

A process for separating a first component of a process stream from a second component of a process stream in a single vessel has been developed. The separation process uses an apparatus having a distillation zone to separate a first component from a second component of a process stream, thereby producing a distillation zone overhead stream enriched in the first component, and a membrane separation zone containing a membrane capable of selectively removing additional amounts of the second component from the distillation overhead stream. The benefit is the production of a high purity process at lower capital equipment costs.

10 Claims, 2 Drawing Sheets

CONTINUOUS DISTILLATION AND MEMBRANE PROCESS

FIELD OF THE INVENTION

The present invention relates to a process for separating a process stream into a first component and a second component using an apparatus which combines both distillation by fractionation and membrane separation by vapor permeation in a single vessel. More specifically, the present invention uses an apparatus having at least one distillation zone to remove at least a portion of the second component and a membrane separation zone containing a membrane capable of selectively removing at least a portion of the second component.

BACKGROUND OF THE INVENTION

In commercial distillation for the separation of one component or a plurality of components from mixtures containing the same, in many instances it is difficult to secure the desired degree of purity. A leading example of the difficulty of separating one component from another component is the breaking of an azeotrope. An azeotropic mixture is defined as a liquid mixture of two or more substances which act as a single substance in that the vapor produced by partial evaporation of the liquid has the same composition as the liquid. The separation of the substances becomes very difficult and expensive.

Azeotropic distillation has been used in the past to circumvent the problems caused when two substances form an azeotropic mixture. In this type of distillation, another substance is added to the azeotropic mixture in order to form another azeotropic mixture with one or more substances of the original mixture. The azeotrope or azeotropes thus formed will have boiling points which differ from the boiling points of the original mixture and will permit greater ease of separation. A problem with azeotropic distillation is that the process where another substance is added to a mixture of substances which need to be separated is not a very efficient process.

Huang et al. U.S. Pat. No. 4,906,787 discloses a process for producing diisopropyl ether containing negligible levels of contaminants (alcohol and water) which comprises hydrating propylene in the presence of an acidic zeolite. The result is an aqueous mixture of ether and alcohol. This aqueous mixture is then passed into a distillation unit operated at conditions which are effective to provide an azeotropic overhead fractionation comprising ether and minor amounts of alcohol and water. The azeotropic overhead fractionation is then passed to an alcohol separation unit which comprises an extraction column that uses process feedwater as the extraction medium. Huang et al. also teaches that the alcohol separation unit can be in the form of a decanter with the condensed azeotropic overheads separating into an ether-rich upper phase and an aqueous alcohol lower phase.

Ladisch et al. U.S. Pat. No. 4,345,973 discloses the recovery of ethanol from a fermentation broth comprising the steps of distilling a dilute aqueous alcohol to form an azeotropic mixture, distilling the azeotropic mixture using a third component consisting of either an organic solvent or a strong salt solution to break the azeotrope and to remove the remaining water, and distilling the resulting mixture to separate water from this third component.

Chen et al. U.S. Pat. No. 4,774,365 discloses a process for producing methyl tertiary butyl ether (MTBE). In the Chen et al. process, excess methanol and isobutylene are fed to an etherification reactor to produce an etherification reactor effluent comprising MTBE, methanol and isobutylene. This excess methanol tends to form azeotropes with MTBE and isobutylene. To circumvent the azeotrope problem, the etherification effluent stream is passed to a pervaporation membrane to separate the methanol into a methanol-rich permeate vapor stream and an ether-rich raffinate stream. The methanol-rich permeate vapor stream is further cooled and compressed to recover the methanol. The ether-rich raffinate stream is sent to a distillation tower to separate the ether from the isobutylene.

Pasternak U.S. Pat. No. 5,160,046 discloses a membrane separation process. In the Pasternak process, an aqueous stream containing an organic oxygen-containing component is contacted with a pervaporation membrane consisting of a polyimine polymer layer which has been interfacially crosslinked with a polyisocyanate linking agent to produce a permeate stream of decreased content of organic oxygen-containing component and a retenate stream of increased content of organic oxygen-containing component. Pasternak teaches that the process can be employed first and followed by distillation.

There is a need for a process using an apparatus that separates a process stream into a stream comprising a substantial portion of a first component and another stream comprising a substantial amount of a second component which apparatus combines the physical separation processes of distillation by fractionation and membrane separation by vapor permeation in a single vessel.

SUMMARY OF THE INVENTION

The present invention solves the above-identified problem by using an apparatus that combines the physical processes of distillation by fractionation and membrane separation by vapor permeation in a single vessel to separate a process stream into a first stream comprising a first component and a second stream comprising a second component. The vessel has at least one distillation zone for removing a component and at least one membrane separation zone containing a membrane capable of selectively removing a component. The distillation zone can be positioned upstream or downstream of the membrane separation zone. The first and second components can be made of single or multiple constituents.

The present invention is a process for separating a process stream into at least a first component and a second component in a single vessel having a distillation zone and a membrane separation zone in fluid communication with the distillation zone, comprising the steps of: passing at least a portion of the process stream into the distillation zone to separate the process stream into a distillation zone overhead stream comprising a substantial amount of the first component and a distillation zone bottoms stream comprising a substantial amount of the second component; passing at least a portion of the distillation zone overhead stream to the membrane separation zone to separate the distillation zone overhead stream into a membrane separation zone overhead stream comprising a substantial amount of any first component contained in the distillation zone overhead stream, the membrane separation zone containing a membrane capable of selectively removing the second component from the distillation zone overhead stream.

In one embodiment, the present invention is a process for separating an alcohol from a process stream comprising the alcohol and water in a single vessel having a lower distillation zone, a membrane separation zone in fluid communication with and positioned upstream of the lower distillation zone, and an upper distillation zone in fluid communication with and positioned upstream of the membrane separation zone comprising the steps of: passing at least a portion of the process stream into the lower distillation zone to separate the process stream into a lower distillation zone overhead stream comprising a substantial amount of the alcohol and a lower distillation zone bottoms stream comprising a substantial amount of the water; passing at least a portion of the lower distillation zone overhead stream to the membrane separation zone to separate the lower distillation zone overhead stream into a membrane separation zone overhead stream comprising a substantial amount of any alcohol contained in the lower distillation zone overhead stream, the membrane separation zone containing a polyimide membrane for selectively removing water from the lower distillation zone overhead stream; and passing at least a portion of the membrane separation zone overhead stream to the upper distillation zone to remove a substantial amount of any water contained in the membrane separation zone overhead.

In another embodiment, the present invention is a process for separating isopropyl alcohol from a process stream comprising isopropyl alcohol and water in a single vessel having a distillation zone and a membrane separation zone in fluid communication with and positioned upstream of the distillation zone, comprising the steps of: passing at least a portion of the process stream into the distillation zone to separate the process stream into a distillation zone overhead stream comprising a substantial amount of the isopropyl alcohol and a distillation zone bottoms stream comprising a substantial amount of the water; and passing at least a portion of the distillation zone overhead stream to the membrane separation zone to separate the distillation zone overhead stream into a membrane separation zone overhead stream comprising a substantial amount of any isopropyl alcohol contained in the distillation zone overhead stream, the membrane separation zone containing a polyimide membrane for selectively removing water from the distillation zone overhead stream.

In still another embodiment, the present invention is a process for separating isopropyl alcohol from a process stream comprising isopropyl alcohol and water in a single vessel having a lower distillation zone, a membrane separation zone in fluid communication with and positioned upstream of the lower distillation zone, and an upper distillation zone in fluid communication with and positioned upstream of the membrane separation zone comprising the steps of: passing at least a portion of the process stream into the lower distillation zone to separate the process stream into a lower distillation zone overhead stream comprising a substantial amount of the isopropyl alcohol and a lower distillation zone bottoms stream comprising a substantial amount of the water; passing at least a portion of the lower distillation zone overhead stream to the membrane separation zone to separate the lower distillation zone overhead stream into a membrane separation zone overhead stream comprising a substantial amount of any isopropyl alcohol contained in the lower distillation zone overhead stream, the membrane separation zone containing a polyimide membrane for selectively removing water from the lower distillation zone overhead stream; and passing at least a portion of the membrane separation zone overhead stream to the upper distillation zone to remove a substantial amount of any water contained in the membrane separation zone overhead.

In yet another embodiment, the present invention is a two-stage process for producing diisopropyl ether using a single vessel having a distillation zone and a membrane separation zone in fluid communication with the distillation zone, comprising the steps of: in a first stage, reacting a propylene-containing stream with isopropyl alcohol in the presence of an etherification catalyst in a diisopropyl ether formation reactor under conditions sufficient to produce a diisopropyl ether formation reactor effluent stream comprising diisopropyl ether, propylene, and isopropyl alcohol; passing at least a portion of the diisopropyl ether formation reactor effluent stream to a light ends recovery zone to separate the diisopropyl ether formation reactor effluent stream into a light ends recovery zone overhead stream comprising a substantial amount of the propylene and a light ends recovery zone bottoms stream comprising a substantial amount of any diisopropyl ether and isopropyl alcohol contained in the diisopropyl ether formation reactor effluent stream; passing at least a portion of the light ends recovery zone bottoms stream to a water wash zone wherein the light ends recovery zone effluent stream is contacted with water in a countercurrent manner to separate the light ends recovery zone effluent stream into a raffinate comprising product diisopropyl ether and an extract comprising isopropyl alcohol and water; in a second stage, reacting at least a portion of the raffinate with water in the presence of a hydration catalyst in an isopropyl alcohol formation reactor under conditions sufficient to produce an isopropyl alcohol formation reactor effluent stream comprising water and isopropyl alcohol; passing at least a portion of the isopropyl alcohol formation reactor effluent stream and at least a portion of the extract to the distillation zone to form a distillation zone overhead stream comprising a substantial amount of the isopropyl alcohol and a distillation zone bottoms stream comprising a substantial amount of the water; passing at least a portion of the distillation zone overhead stream to the membrane separation zone to separate the distillation overhead stream into a membrane separation zone overhead stream comprising a substantial amount of any isopropyl alcohol contained in the distillation zone overhead stream, the membrane separation zone containing a membrane capable of selectively removing the water from the distillation zone overhead stream; and passing at least a portion of the membrane separation zone overhead stream to the diisopropyl ether formation reactor.

In another embodiment, the present invention is a two-stage process for producing diisopropyl ether using a cylindrical vessel having a distillation zone and a membrane separation zone in fluid communication with and positioned upstream of the distillation zone, comprising the steps of: in a first stage, reacting a propylene-containing stream with isopropyl alcohol in the presence of an etherification catalyst in a diisopropyl ether formation reactor under conditions sufficient to produce a diisopropyl ether formation reactor effluent stream comprising diisopropyl ether, propylene, and isopropyl alcohol; passing at least a portion of the diisopropyl ether formation reactor effluent stream to a light ends recovery zone to separate the diisopropyl ether formation reactor effluent stream into a light ends recovery zone overhead stream comprising a substantial amount of the propylene and a light ends recovery zone bottoms stream comprising a substantial amount of the diisopropyl ether and isopropyl alcohol; passing at least a portion of the light ends recovery zone bottoms stream to a water wash zone wherein the light ends recovery zone effluent stream is contacted with water in a countercurrent manner to separate the light ends recovery zone effluent stream into a raffinate comprising product diisopropyl ether and an extract comprising isopropyl alcohol and water; in a second stage, reacting at least a portion of the raffinate with water in the presence of a hydration catalyst in an isopropyl alcohol formation reactor under conditions sufficient to produce an isopropyl alcohol formation reactor effluent stream comprising water and isopropyl alcohol; passing at least a portion of the isopropyl alcohol formation reactor effluent stream and at least a portion of the extract to the distillation zone to form a distillation zone overhead stream comprising a substantial amount of the isopropyl alcohol and a distillation zone bottoms stream comprising a substantial amount of the water; passing at least a portion of the distillation zone overhead stream to the membrane separation zone to separate the distillation overhead stream into a membrane separation zone overhead stream comprising a substantial amount of any isopropyl alcohol contained in the distillation zone overhead stream, the membrane separation zone containing a polyimide membrane capable of selectively removing the water from the distillation zone overhead stream; and passing at least a portion of the membrane separation zone overhead stream to the diisopropyl ether formation reactor.

In still another embodiment, the present invention is a two-stage process for producing diisopropyl ether using a cylindrical vessel having a lower distillation zone, a membrane separation zone in fluid communication with and positioned upstream of the lower distillation zone, and an upper distillation zone in fluid communication with and positioned upstream of the membrane separation zone, comprising the steps of: in a first stage, reacting a propylene-containing stream with isopropyl alcohol in the presence of an etherification catalyst in a diisopropyl ether formation reactor under conditions to produce a diisopropyl ether formation reactor effluent stream comprising diisopropyl ether, propylene, and isopropyl alcohol; passing at least a portion of the diisopropyl ether formation reactor effluent stream to a light ends recovery zone to separate the diisopropyl ether formation reactor stream into a light ends recovery zone overhead stream comprising a substantial amount of the propylene and a light ends recovery zone bottoms stream comprising a substantial amount of the diisopropyl ether and isopropyl alcohol; passing at least a portion of the light ends recovery zone bottoms stream to a water wash zone wherein the light ends recovery zone effluent stream is contacted with water in a countercurrent manner to separate the light ends recovery zone effluent stream into a raffinate comprising product diisopropyl ether and an extract comprising isopropyl alcohol and water; in a second stage, reacting at least a portion of the raffinate with water in the presence of a hydration catalyst in an isopropyl alcohol formation reactor under conditions sufficient to produce an isopropyl alcohol formation reactor effluent stream comprising water and isopropyl alcohol; passing at least a portion of the isopropyl alcohol formation reactor effluent stream and at least a portion of the extract to the distillation zone to form a distillation zone overhead stream comprising a substantial amount of the isopropyl alcohol and a distillation zone bottoms stream comprising a substantial amount of the water; passing at least a portion of the distillation zone overhead stream to the membrane separation zone to separate the distillation overhead stream into a membrane separation zone overhead stream comprising a substantial amount of any isopropyl alcohol contained in the distillation zone overhead stream, the membrane separation zone containing a polyimide membrane capable of selectively removing the water from the distillation zone overhead stream; passing at least a portion of the membrane separation zone overhead stream to the upper distillation zone to produce an upper distillation zone bottoms stream comprising a substantial amount of any isopropyl alcohol contained in the membrane separation zone overhead stream; and passing at least a portion of the upper distillation zone bottoms stream to the diisopropyl ether formation reactor.

DESCRIPTION OF THE PREFERRED EMBODIMENT

The present invention is a process for separating a process stream into at least a first component and a second component in a single vessel having a distillation zone and a membrane separation zone in fluid communication with the distillation zone. The process steps comprise: (1) passing at least a portion of the process stream into the distillation zone to separate the process stream into a distillation zone overhead stream comprising a substantial amount of the first component and a distillation zone bottoms stream comprising a substantial amount of the second component; and (2) passing at least a portion of the distillation zone overhead stream to the membrane separation zone to separate the distillation zone overhead stream into a membrane separation zone overhead stream comprising a substantial amount of any first component contained in the distillation zone overhead stream. The membrane separation zone contains a membrane capable of selectively removing the second component from the distillation zone overhead stream. As used herein, "substantial" is defined as greater than about 75 mass %, preferably greater than about 85 mass %, most preferably greater than about 95 mass %.

The process stream of the present invention can be any stream which contains at least two components. For example, the stream could be a mixture of an alcohol such as ethanol, isopropyl alcohol, n-propyl alcohol, sec-butyl alcohol, or cyclohexanol, and water. Each component may be a single constituent or a plurality of constituents. In one embodiment of the present invention, the process stream is a mixture or an azeotrope of alcohol and water with the first component being the alcohol and the second component being the water. A specific embodiment of the invention is one where the first component is a mixture or an azeotrope of diisopropyl ether (DIPE) and isopropyl alcohol (IPA) and the second component is water.

The present invention uses a vessel that has at least one distillation zone and at least one membrane separation zone. In the distillation zone, the process stream is separated by fractionation into a distillation zone overhead stream comprising a substantial amount of the first component and a distillation zone bottoms stream comprising a substantial amount of the second component.

The operating conditions for the distillation zone will vary depending on the relative composition of the process stream and the desired first component purity. The distillation zone can contain trays, plates, and packing to assist in the separation. The distillation zone can also contain a catalyst for separating the first component from the second component, and/or a catalyst for reacting the first component in the presence of catalyst to form a third component.

The membrane separation zone serves to separate the distillation zone overhead stream into a membrane separation zone overhead stream comprising a substantial amount of the first component contained in the distillation zone overhead stream. The membrane in the membrane separation zone is preferably a hollow tube type membrane where the membrane defines hollow portions, or internal passages, which have means for adding fluids to said internal passages and means for withdrawing fluids from said internal passages, and is capable of separating at least one first component from a second component by vapor permeation. For example, at least one of the components contained in the distillation overhead stream would have a very low rate of permeation through the membrane and into the internal passage and therefore would remain in the vessel to be contained in the membrane overhead stream. Or, in other words, only select components would have a high rate of permeation through the membrane and into the internal passage of the membrane to be conducted from the vessel through the internal passage via a carrier fluid and therefore be removed from the membrane overhead stream. By maintaining a partial pressure differential across the membrane, which is usually a pressure drop from about 1 to about 50 psia, the first component preferentially permeates the membrane, thereby moving from the exterior of the membrane into the internal passage of the membrane. The interior side of the membrane can be equipped with a pressure decreasing means which is usually a carrier fluid in order to decrease the pressure on the interior side and achieve better diffusion of the permeate through the membrane. The carrier fluid also serves to sweep the components through the internal passages of the membrane and remove them from the vessel. The carrier fluid may be compounds such as nitrogen, hydrogen, helium, or low carbon number hydrocarbons such as propane and butane. Typically the carrier fluid is heated prior to being introduced into the internal passage to prevent components from condensing in the internal passage.

The membrane separation zone may consist of one or more units which in turn may consist of a single membrane device or, alternatively, several membrane devices integrated and operated so as to achieve the separation in the most efficient manner, for example, a cascade of membrane bundles with an internal recycle stream between various stages of the membrane unit. In one embodiment of the present invention, the membrane separation zone consists of modules, each having certain membrane areas for permeation and also appropriate heat exchangers to compensate for the cooling effect due to permeation. The operating pressure of the membrane unit can range from about 1 to about 150 psig, or higher, and the temperature from about 35° F. to about 300° F.

The membrane used in the membrane separation zone can be any composite suitable for use in separating alcohols from water by vapor permeation including, but are not limited to, a nonporous polyimine, preferably a polyimine which has been interfacially crosslinked with a polyisocyanate or with a poly(carbonyl) chloride, a polyacrylonitrile polymer, a polysulfone polymer, a film of perfluorosulfonic acid polymer on a porous matrix polytetrafluoroethylene, a polyvinyl alcohol and a polyacrylic acid on a polyacrylonitrile support layer. Suitable physical characteristics for the membrane include a thickness of about 5 to about 80 microns and a molecular weight limit of about 40,000 to about 50,000.

The preferred membrane is a polyimide membrane with an asymmetric structure. Such a membrane should have excellent chemical tolerance and high thermal stability and selectivity. The polyimide membrane is produced by the condensation polymerization of biphenyltetracarboxylic dianhydride and aromatic diamines. Its chemical structure is:

where Ar is a divalent aromatic radical. The polyimide membrane is a type of hollow fiber with an asymmetric structure having a dense layer on a microporous support. The dense layer serves to separate a gas mixture and is designed to be ultrathin in order to obtain a practical permeation rate. The microporous support of the membrane reinforces the dense layer and has a minimum effect on the gas separation. The hollow fiber is uniformly made in a one-step process from the polyimide dope and is wholly made of the same material.

In one embodiment of the present invention, the membrane component is a membrane assembly including a carrier layer which provides mechanical strength, a porous support layer, and a separating layer across which separation occurs. The carrier layer is typically characterized by a high degree of porosity and mechanical strength. It may be fibrous or nonfibrous, woven or nonwoven. The porous support layer can be a polyacrylonitrile or polysulfone polymer. The separating layer can be a nonporous film or membrane, e.g., a polyimide polymer crosslinked by urea or amide linkages. The physical arrangement of the zones within the vessel can be such that the distillation known is upstream or downstream of the membrane separation zone.

In a preferred embodiment, the apparatus used in the process of the present invention is a cylindrical vessel consisting of a lower distillation zone, a membrane separation zone positioned upstream of and in fluid communication with the lower distillation zone, and an upper distillation zone positioned upstream of and in fluid communication with the membrane zone.

The invention is best explained in terms of the specific embodiment where the stream to be separated is a mixture of IPA and water with the first component being the IPA and the second component being the water. Typically, the IPA and water mixture will be the effluent from an IPA production process, and the water will be present in an excess amount. Commonly expected concentrations are, for example, 82 mass % water and 18 mass % IPA. The present invention, by requiring only a single vessel, significantly reduces both capital costs and operational costs of the separation incurred in separating IPA and water as compared with the two-unit systems, usually an azeotrope column and a distillation column, currently used in industry.

The stream containing the IPA and water mixture is introduced into the distillation zone where a majority of the water is easily separated by fractionation and removed from the IPA in a distillation zone bottoms stream due to the difference in boiling points of the water and the alcohol. As the concentration of water in the mixture decreases, an azeotrope of 88 mass % IPA and 12 mass % water will form and additional water will not be separated from the azeotrope in the distillation zone. The distillation overhead stream then encounters the membrane in the membrane separation zone which is, e.g., a polyimide hollow fiber membrane capable of selectively removing water from the distillation overhead stream. A portion of the water present in the distillation overhead stream permeates the membrane and enters into the internal passage of the polyimide hollow fiber membrane and is conducted through the internal passage and out of the system using a heated carrier fluid thereby causing the concentration of water in the membrane overhead to fall below that required to maintain the azeotrope. Or, in other words, the IPA, which has a comparatively low rate of permeation into the internal passage of the hollow fiber membrane, is retained in the system and forms the main component for the membrane overhead stream. In this embodiment of the invention, the membrane and the operating conditions are chosen so that sufficient water is removed to result in a membrane overhead stream containing at least 98 mass % isopropyl alcohol which is then removed from the vessel and collected.

Removing sufficient water to provide a stream of at least 98 mass % IPA may be difficult, so another embodiment of the invention is one where only a portion of the water available is removed in the membrane separation zone, and a second distillation zone is employed to separate any alcohol and water azeotrope from the alcohol. In general terms, the embodiment involves (1) distilling in the lower distillation zone a process stream into a lower distillation zone overhead stream enriched in a first component and a lower distillation zone bottoms stream enriched in a second component; (2) conducting the lower distillation zone overhead stream to the membrane separation zone and selectively removing a portion of the second component from the lower distillation zone overhead stream to afford a membrane separation zone overhead stream which is depleted in the second component; (3) passing the membrane separation zone overhead stream to the upper distillation zone and distilling to form an upper distillation zone bottoms stream containing at least 98 mass % first component and an upper distillation zone overhead stream; and (4) collecting the upper distillation zone bottoms stream from the upper distillation zone.

As applied to the specific embodiment where the stream to be separated is a mixture of IPA and water with the first component being the alcohol and the second component being the water, the invention would proceed as follows. The stream containing the IPA and water mixture is introduced into the lower distillation zone where a majority of the water is easily separated and removed from the IPA in a lower distillation zone bottoms stream due to the difference in boiling points of the water and the alcohol. As the concentration of water in the mixture decreases, an azeotrope of 88 mass % IPA and 12 mass % water will form, and additional water will not be separated from the azeotrope in the distillation zone. The lower distillation zone overhead stream then encounters the membrane separation zone where additional water may be removed by the membrane causing the concentration of water to fall below that required to maintain the azeotrope. In this embodiment, the membrane separation zone is operated so that only a portion of the available water is removed resulting in a membrane separation zone overhead stream requiring further distillation. The water-depleted membrane separation zone overhead stream is then introduced to an upper distillation zone where IPA may be separated from the IPA and water azeotrope that reforms with the removal of IPA due to the slight yet sufficient difference in the boiling points of the alcohol and the azeotrope. A upper distillation zone bottoms stream of at least 98 mass % IPA may be collected, and the upper distillation zone overhead stream containing the azeotrope may be recycled to the lower distillation zone.

Applicant has found that when using the two distillation zone embodiment, it is preferred that the vessel have a physical barrier between the membrane separation zone and the upper distillation zone. The effluent from the membrane separation zone is conducted in a line external to the vessel and is introduced to the upper distillation zone at least a short distance from the beginning of the upper distillation zone. For example, when the distillation zone is comprised of a series of trays, the membrane separation zone effluent should be introduced at least two trays into the upper distillation zone. The stream containing substantially the first component is withdrawn from the upper distillation zone in the portion of the upper distillation zone after the beginning of the second distillation zone and before the introduction of the membrane separation zone effluent. Since the membrane separation zone effluent is introduced at a point after the withdrawal of the first component stream, there is less opportunity for mixing, and the concentration of the first component in the first component stream is higher. Of course, a conduit allowing for non-removed liquid to pass to the membrane separation zone may be provided.

In another embodiment of the present invention, the separation process of the present invention is incorporated into a two-stage DIPE producing process to assist in breaking the IPA-water azeotrope that is formed during the production of DIPE. In the first stage of the two-stage DIPE process, a propylene-containing stream is passed to a first stage DIPE formation reactor and reacted with recycled IPA to form DIPE in the presence of an etherification catalyst.

The propylene-containing stream can include, but is not limited to, gas plant off-gas containing propylene, naphtha cracker off-gas containing light olefins, and refinery fluidized catalytic cracked (FCC) propane/propylene streams. The concentration of propylene used will vary depending upon the source of the propylene. These sources provide a propylene/propane mixture comprising about 60 to about 80 vol. % propylene. In a preferred embodiment, the propylene concentration of the propylene-containing stream is less than about 70 vol. %.

The etherification catalyst can be any catalyst suitable for propylene conversion. Suitable etherification catalysts include zeolites and ion exchange resins. With respect to zeolites, both intermediate and large pore zeolites can be used. Of particular interest for use herein are large pore acidic zeolites, e.g. zeolite Beta, X, L, Y, ultra stable Y, rare earth Y, ZSM-3, ZSM-4, ZSM-12, ZSM-20, and ZSM-50.

With respect to the ion exchange resin, a synthetic ion exchange resin is preferred. The preferred ion exchange resin has three components: (1) the raw material which is used for the construction of the skeleton or matrix; (2) bridging agents for cross-linking and insolubilization; and (3) the type and number of functional active groups.

With respect to forming the ion exchange resin matrix, polymerization and polycondensation can be used as the synthesis route. Polymerization is preferred because the matrices resulting therefrom generally have higher chemical and thermal stability. The preferred starting material for synthesizing the catalyst of the present invention is styrene. The styrene is polymerized with itself and with divinylbenzene into a polymeric molecule:

Matrices for the catalyst of the present invention can also be prepared using: (1) a divinylbenzene and an acrylic acid or methacrylic acid or;

(2) phenol and formaldehyde;

In the case of divinylbenzene-containing matrices, crosslinking depends on the quantity of divinylbenzene used as the crosslinking agent. The nature and degree of crosslinking can have a profound effect on the ion exchange properties of the catalyst. The amount of divinylbenzene used can range from about 2 to 12 wt. %. With respect to the structure of the network of synthetic ion exchange resins, different types are now available with designations such as gel, macroporous, and isoporous ion exchange resins. With respect to gel-type ion exchange resins, during polymerization of styrene and divinylbenzene, the network formed is obtained as a gel. The properties of such a co-polymer can be varied by changing the ratios of the amounts of the individual monomers used during the synthesis. These gel-type polymer structures have no appreciable porosity until they are swollen in suitable medium, but such crosslinked polymers swell to a well-defined and reproducible degree in an appropriate solvent system, such as toluene. Macroporous ion exchange resins are types in which a solvent is used during production from the monomers so that a porous matrix structure is formed in the course of polymerization. The isoporous ion exchange resins are a group in which the crosslinking and pore size are modified in a way to obtain polymers with a substantially uniform pore size.

In a preferred embodiment, the first stage DIPE formation catalyst is a cation exchange resin comprising $SO_3H$ groups. Suitable cation exchange resins include, for example, sulfonated organic resins in their acidic form. Of particular importance are sulfonated polystyrene resins, such as the $SO_3H$ groups containing co-polymers of aromatic monovinyl compounds and aromatic polyvinyl compounds. Especially preferred cation exchange resins are sulfonated styrene/divinylbenzene co-polymers, for example, "Amberlyst 36." These cation exchange resins are produced by the sulfonation of suspension co-polymer beads with sulfuric acid, sulfur trioxide, fuming surfuric acid or chlorosulfonic acid. The $SO_3$ groups which are the ionic groups yielding the cation exchange function can be in the para position.

The etherification catalyst can have a surface area of about 1 to about 100 $m^2/g$, preferably approximately 35 and a porosity of about 0.05 to 0.5 ml/g, preferably 0.30 ml/g.

Suitable conditions for the first stage DIPE formation reactor include a temperature of about 200° to about 300° F., a pressure of about 100 to about 1200 psig, preferably about 700 to about 1000 psig, and an IPA to propylene ratio of about 0.1:1 to about 2:1, preferably about 0.6:1.

In the first stage reactor, etherification can be carried out under liquid phase, vapor phase or mixed vapor-liquid phase conditions in a batch or continuous manner. With respect to the first stage DIPE formation reactor, a stirred tank reactor or fixed bed reactor can be employed. The flow of reactants and products can be liquid-upflow, liquid-downflow, countercurrent, or cocurrent, having a liquid hourly space velocity of about 0.1 to 20, preferably about 0.1 to 2 when operating in the continuous mode. In a preferred embodiment, the single stage reactor can be a liquid phase fixed-bed reactor with recirculation of cooled etherification zone effluent for temperature control.

Effluent containing DIPE, IPA, propylene, and propane from the first stage DIPE formation reactor is passed to a light ends recovery zone where propylene and propane are removed.

Effluent from the light ends recovery zone is passed to a water wash zone where IPA is removed to produce an extract comprising residual IPA and water and a raffinate stream comprising a DIPE product stream.

Regardless of whether the first stage effluent stream is treated to remove light ends or residual IPA, at least a portion of the DIPE product stream is passed to a second stage IPA formation reactor where DIPE is reacted with water in the presence of a hydration catalyst under conditions sufficient to produce a second stage effluent stream comprising IPA, water and a small amount of DIPE.

The hydration catalyst suitable for use in the IPA formation reactor is the same as the etherification catalyst described above, although a catalyst which is more suitable for reaction with high levels of water and at hotter temperatures is preferred.

Suitable conditions for the IPA formation reactor include a temperature of about 250° to about 350° F., a pressure of about 100 to about 500 psig, preferably about 300 to about 400 psig, and a water to DIPE ratio of about 1:1 to about 50:1, preferably about 10:1.

In the IPA formation reactor, hydration of DIPE can be carried out under dense phase, liquid phase, vapor phase or mixed vapor-liquid phase conditions in a batch or continuous manner. Further, with respect to the IPA formation reactor, a stirred tank reactor or fixed bed reactor can be employed. The flow of reactants and products can be trickle-bed, liquid-upflow, liquid-downflow, countercurrent, or cocurrent having a liquid hourly space velocity of about 0.05 to 20, preferably about 0.1 to 2 when operating in the continuous mode.

The effluent stream from the IPA formation reactor and the extract from the water wash zone are both treated by the separation process of the present invention. In this separation process, the IPA formation effluent and the extract from the water wash zone are passed to an apparatus consisting of a cylindrical vessel containing a lower distillation zone, a membrane separation zone in fluid communication with the lower distillation zone and positioned above the lower distillation zone and an upper distillation zone in fluid communication with the membrane zone and positioned upstream of the membrane separation zone. Accordingly, a mixture of water and IPA is fed to the lower distillation zone which separates the mixture into a lower distillation zone overhead stream having an alcohol concentration of at least about 80 mass % and a lower distillation zone bottoms stream having a water concentration of at least about 90 mass %.

The lower distillation zone overhead stream enters the membrane separation zone which contains a polyimide membrane capable of selectively removing water from the lower distillation zone overhead stream. In the membrane separation zone, water contained in the lower distillation zone overhead stream is removed by the membrane.

A membrane separation zone overhead stream exits the membrane zone and enters the upper distillation zone. The upper distillation zone separates the membrane separation zone overhead stream into an upper distillation zone overhead stream having a water and IPA azeotrope and an upper distillation zone bottoms stream having an IPA concentration of at least about 98 mass %. The upper distillation zone overhead stream is recycled to the lower distillation zone and the upper distillation zone bottoms stream containing a substantial amount of the IPA is recycled to the DIPE formation reactor.

Figure 1:
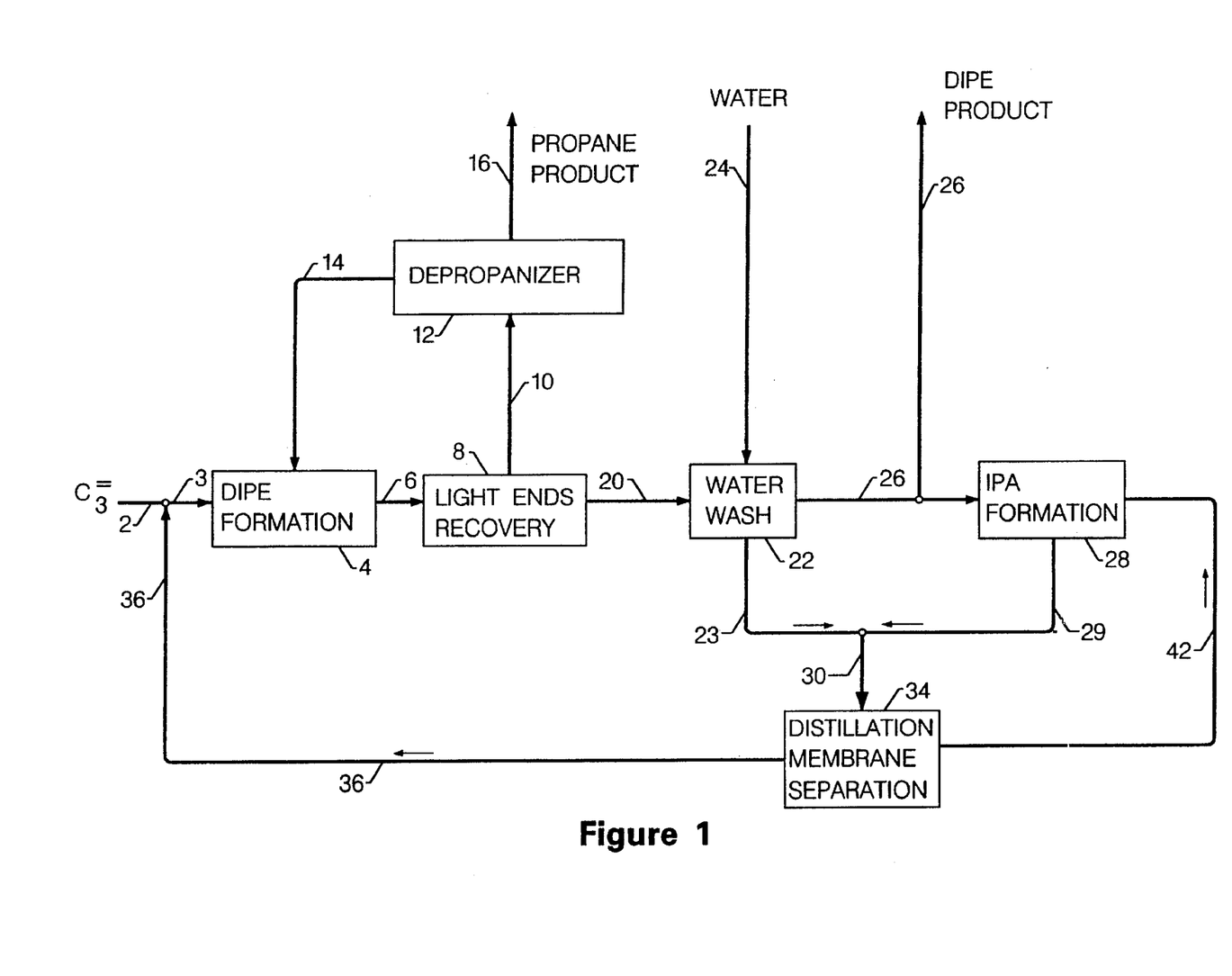
FIG. 1 is a schematic representation of the preferred diisopropyl ether process of the present invention.

Referring to FIG. 1, a propylene-containing stream 2 is contacted with upper distillation zone bottoms stream 36 comprising IPA and having a concentration of less than 3 mass % water. A combined feed is fed to first stage DIPE formation reactor 4 through line 3. In DIPE formation reactor 4, IPA is reacted with propylene to form DIPE at a temperature of about 250° F. and a pressure of about 800 psig.

Exiting DIPE formation reactor 4 is a first stage effluent stream 6 which comprises DIPE and unreacted propylene and IPA. First stage effluent stream 6 is routed to light ends recovery zone 8 for removal of light ends, i.e., propylene and propane. In light ends recovery zone 8, propane and propylene are removed from first stage effluent stream 6 at a temperature of about 113° to about 350° F. and a pressure of about 240 psig.

A propylene/propane overhead mixture exits the top of light ends recovery zone 8 in stream 10 and enters depropanizer 12. Depropanizer 12 is operated at a temperature of about 135° F. and a pressure of about 295 to about 305 psig. A propylene recycle stream 14 rich in propylene and containing a small amount of propane is removed from the top of depropanizer 12 and passed to DIPE formation reactor 4. A propane product stream 16 exits depropanizer 12.

Effluent from light ends recovery zone 8 is sent to water wash zone 22 via line 20. In water wash zone 22, water entering zone 22 through stream 24 is contacted countercurrently with the light ends recovery zone effluent stream for the purpose of removing small amounts of IPA from the light ends recovery zone effluent stream. Exiting water wash zone 22 in line 26 essentially free of IPA is a raffinate stream comprising product DIPE. An extract stream comprising IPA and water exits the bottom of water wash zone 22 in stream 23 and is passed to apparatus 34.

At least a portion of the DIPE product stream 26 is passed to second stage IPA formation reactor 28 where DIPE is hydrated to form isopropyl ether. Exiting IPA formation reactor 28 in line 29 is the second stage effluent stream comprising IPA, DIPE and water.

Figure 2:
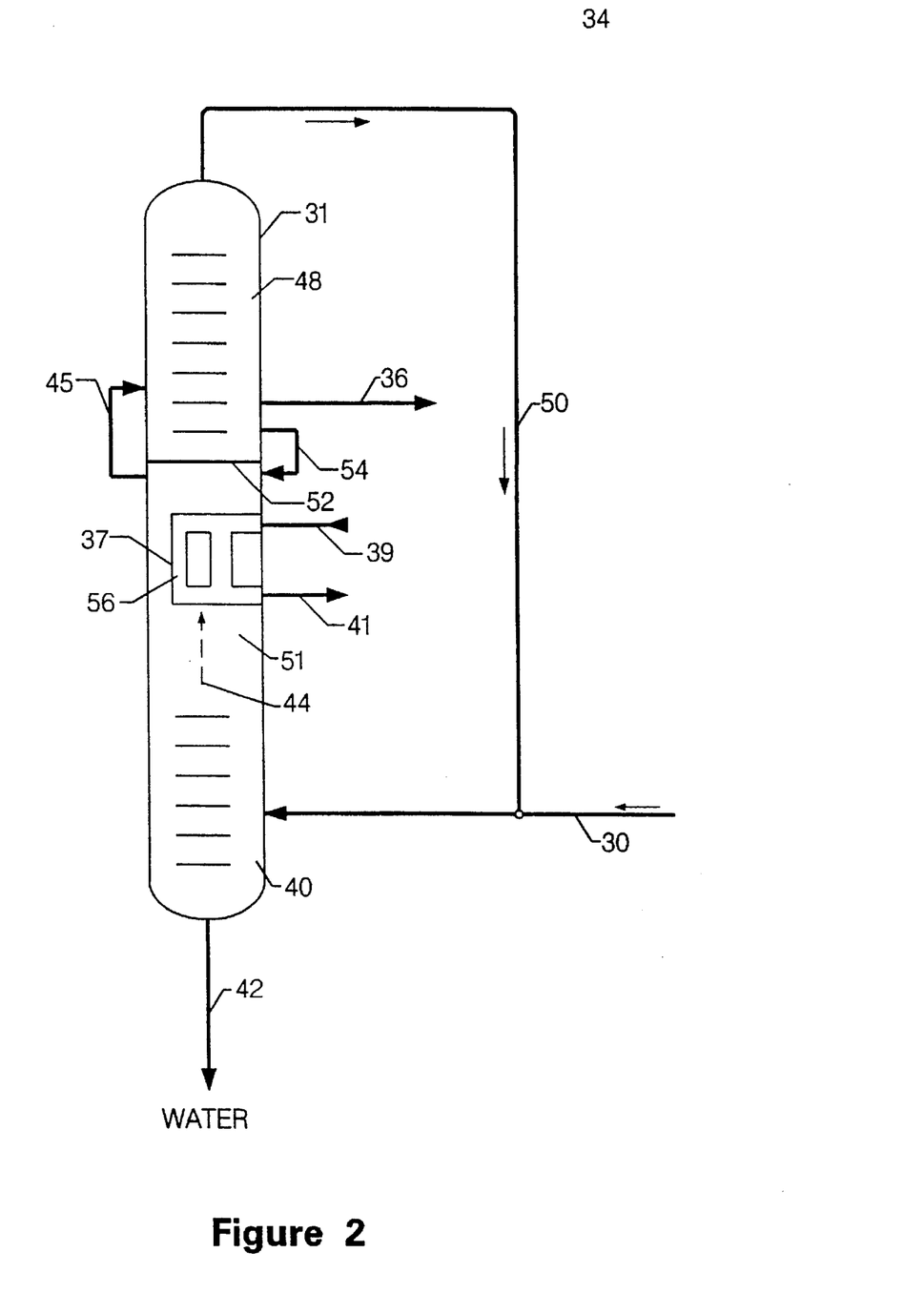
FIG. 2 is a schematic representation of the apparatus used in the preferred diisopropyl ether process of the present invention.

The second stage effluent stream is passed to apparatus 34. Referring to FIG. 2, apparatus 34 consists of cylindrical vessel 31 containing three major operating zones: (1) lower distillation zone 40; (2) membrane separation zone 51 positioned above the lower distillation zone 40 and in fluid communication with lower distillation zone 40; and (3) upper distillation zone 48 positioned above the membrane separation zone 51 and in fluid communication with membrane separation zone 51.

The lower distillation zone 40 is the position along the length of the vessel 31 where extract stream 23 and the second stage effluent stream 29 are introduced through combined feed 30. The concentration of this feed stream 30 is about 50 mass % water and 50 mass % IPA. Exiting lower distillation zone 40 is a lower distillation zone bottoms stream 42 comprising a substantial amount of water removed from the second stage effluent stream. A lower distillation zone overhead stream 44, an azeotropic mixture of IPA and water, exits lower distillation zone 40 and enters membrane separation zone 51.

Membrane separation zone 51 has a hollow fiber type polyimide membrane 37. Stream 39 introduces heated nitrogen carrier gas into the internal passage 56 of the hollow fiber membrane 37. Water has a high rate of permeability into the internal passage 56 of the membrane 37 and is conducted through the internal passage 56 and removed in stream 41. The IPA has a comparatively low rate of permeability into the internal passage 56, and continues through the membrane separation zone 51.

A mixture of IPA and water exits membrane separation zone 51 in membrane separation zone overhead stream 45 which is conducted around physical barrier 52, and enters upper distillation zone 48. In upper distillation zone 48, additional water is removed from the membrane separation zone overhead stream by fractionation. Upper distillation overhead stream 50 exits the top of vessel 31 and is recycled to combine with feed stream 30. The upper distillation zone bottoms stream 36 exits upper distillation zone 48 and is recycled to DIPE formation reactor 4. Note that the point at which the upper distillation zone bottoms stream is removed is between the beginning of upper distillation zone 8 and the introduction of the membrane separation zone overhead stream 45. Line 54 is provided to allow excess liquid to pass to membrane separation zone 51.

What is claimed is:

1. A process, conducted in a single vessel having a distillation zone and a membrane separation zone in fluid communication therewith, for separating an alcohol from a mixture containing an alcohol and water, comprising the steps of:

(a) separating said mixture in the distillation zone to afford a distillation zone overhead stream containing a substantial amount of said alcohol; and (b) passing at least a portion of the distillation zone overhead stream to the membrane separation zone to afford a membrane separation zone overhead stream containing a substantial amount of any alcohol contained in the distillation zone overhead stream, said membrane separation zone containing a membrane capable of selectively removing the water from the distillation zone overhead stream.

2. The process of claim 1 where the alcohol is selected from the group consisting of ethanol, isopropyl alcohol, n-propyl alcohol, sec-butyl alcohol, and cyclohexanol.

3. The process of claim 1 wherein said distillation zone contains a hydrocarbon conversion catalyst for reactive distillation.

4. The process of claim 1 wherein said membrane separation zone is positioned upstream of said distillation zone.

5. The process of claim 1 wherein said membrane separation zone is positioned downstream of said distillation zone.

6. A process for separating an alcohol from a process stream comprising an alcohol and water in a single vessel having a lower distillation zone and a membrane separation zone in fluid communication with and positioned upstream of said lower distillation zone and an upper distillation zone in fluid communication with and positioned upstream of said membrane separation zone comprising the steps of:

(a) passing at least a portion of said process stream into said lower distillation zone to separate said process stream into a lower distillation zone overhead stream comprising a substantial amount of said alcohol;

(b) passing at least a portion of said lower distillation zone overhead stream to said membrane separation zone to separate said lower distillation zone overhead stream into a membrane separation zone overhead stream comprising a substantial amount of any alcohol contained in said lower distillation zone overhead stream, said membrane separation zone containing a polyimide membrane for selectively removing water from said lower distillation zone overhead stream; and (c) passing at least a portion of said membrane separation zone overhead stream to said upper distillation zone to remove a substantial amount of any water contained in said membrane separation zone overhead stream.

7. The process of claim 6 where the alcohol is selected from the group consisting of ethanol, isopropyl alcohol, n-propyl alcohol, sec-butyl alcohol, and cyclohexanol.

8. The process of claim 6 wherein said distillation zone contains a hydrocarbon conversion catalyst for reactive distillation.

9. A process for separating isopropyl alcohol from a process stream comprising isopropyl alcohol and water in a single vessel having a distillation zone and a membrane separation zone in fluid communication with and positioned upstream of said distillation zone, comprising the steps of:

(a) passing at least a portion of said process stream into said distillation zone to separate said process stream into a distillation zone overhead stream comprising a substantial amount of said isopropyl alcohol; and (b) passing at least a portion of said distillation zone overhead stream to said membrane separation zone to separate said distillation zone overhead stream into a membrane separation zone overhead stream comprising a substantial amount of any isopropyl alcohol contained in said distillation zone overhead stream, said membrane separation zone containing a polyimide membrane for selectively removing water from said distillation zone overhead stream.

10. A process for separating isopropyl alcohol from a process stream comprising isopropyl alcohol and water in a single vessel having a lower distillation zone and a membrane separation zone in fluid communication with and positioned upstream of said lower distillation zone and an upper distillation zone in fluid communication with and positioned upstream of said membrane separation zone comprising the steps of:

(a) passing at least a portion of said process stream into said lower distillation zone to separate said process stream into a lower distillation zone overhead stream comprising a substantial amount of said isopropyl alcohol;

(b) passing at least a portion of said lower distillation zone overhead stream to said membrane separation zone to separate said lower distillation zone overhead stream into a membrane separation zone overhead stream comprising a substantial amount of any isopropyl alcohol contained in said lower distillation zone overhead stream, said membrane separation zone containing a polyimide membrane for selectively removing water from said lower distillation zone overhead stream; and (c) passing at least a portion of said membrane separation zone overhead stream to said upper distillation zone to remove a substantial amount of any water contained in said membrane separation zone overhead stream.

* * * * *